United States Patent
Ferree (10) Patent No.: US 6,419,704 B1
(45) Date of Patent: Jul. 16, 2002

(54) ARTIFICIAL INTERVERTEBRAL DISC REPLACEMENT METHODS AND APPARATUS

(76) Inventor: Bret Ferree, 1238 Cliff Laine Dr., Cincinnati, OH (US) 45208

( * ) Notice: Subject to any disclaimer, the term of this patent is extended or adjusted under 35 U.S.C. 154(b) by 0 days.

(21) Appl. No.: 09/415,382

(22) Filed: Oct. 8, 1999

(51) Int. Cl.⁷ .................................................. A61F 2/44
(52) U.S. Cl. .................................................. 623/17.12
(58) Field of Search ........................ 623/17.11, 17.12, 623/17.16

(56) References Cited

U.S. PATENT DOCUMENTS

| | | | |
|---|---|---|---|
| 2,677,369 A | 5/1954 | Knowles | 128/92 |
| 3,366,975 A | 2/1968 | Pangman | 3/36 |
| 3,426,364 A | 2/1969 | Lumb | 3/1 |
| 3,551,560 A | 12/1970 | Thiele | 424/95 |
| 3,593,342 A | 7/1971 | Niebauer | 3/1 |
| 3,648,294 A | 3/1972 | Shahrestani | 3/1 |
| 3,855,638 A | 12/1974 | Pilliar | 3/1 |
| 3,867,728 A | 2/1975 | Stubstad et al. | 3/1 |
| 3,875,595 A | 4/1975 | Froning | 3/1 |
| 3,883,902 A | 5/1975 | Lynch | 3/36 |
| 4,229,839 A | 10/1980 | Schwemmer | 3/1.91 |
| 4,309,777 A | 1/1982 | Patil | 3/1.91 |
| 4,349,921 A | 9/1982 | Kuntz | 3/1 |
| 4,663,358 A | 5/1987 | Hyon et al. | 521/64 |
| 4,707,872 A | 11/1987 | Hessel | 5/451 |
| 4,714,469 A | 12/1987 | Kenna | 623/17 |
| 4,759,766 A | 7/1988 | Buettner-Janz et al. | 623/17 |
| 4,772,287 A | * 9/1988 | Ray et al. | 623/17.11 |
| 4,863,477 A | * 9/1989 | Monson | 623/17.11 |
| 4,874,389 A | 10/1989 | Downey | 623/17 |
| 4,904,260 A | * 2/1990 | Ray et al. | 623/17.16 |
| 4,911,718 A | 3/1990 | Lee et al. | 623/17 |
| 4,917,704 A | 4/1990 | Frey et al. | 623/17 |
| 4,932,969 A | 6/1990 | Frey et al. | 623/17 |
| 4,946,378 A | 8/1990 | Hirayama et al. | 623/17 |
| 5,002,576 A | 3/1991 | Furhmann et al. | 623/17 |
| 5,035,716 A | 7/1991 | Downey | 623/17 |
| 5,047,055 A | 9/1991 | Bao et al. | 623/17 |
| 5,071,437 A | 12/1991 | Steffee | 623/17 |
| 5,108,438 A | 4/1992 | Stone | 623/17 |
| 5,123,926 A | 6/1992 | Pisharodi | 623/17 |
| 5,171,280 A | 12/1992 | Baumgartner | 623/17 |
| 5,171,281 A | 12/1992 | Parsons et al. | 623/17 |
| 5,192,326 A | 3/1993 | Bao et al. | 623/17 |
| 5,246,458 A | 9/1993 | Graham | 623/17 |
| 5,258,031 A | 11/1993 | Salib et al. | 623/17 |
| 5,258,043 A | 11/1993 | Stone | 623/66 |
| 5,314,477 A | 5/1994 | Marnay | 623/17 |

(List continued on next page.)

Primary Examiner—David H. Willse
Assistant Examiner—Suzette J. Jackson
(74) Attorney, Agent, or Firm—Gifford, Krass, Groh, Sprinkle, Anderson & Citkowski, PC (57) ABSTRACT

Artificial disc replacements for natural intervertebral discs make use of a shaped body having a final volume sized to consume at least a portion of an intervertebral disc space, and a filling within the shaped body enabling the body to cyclically compress and expand in a manner similar to the disc material being replaced. The filling may be a gas, liquid or a gel, in which case the body further includes valve means enabling the body to be filled, preferably following introduction into the disc space. Depending upon the application and other factors, one or more of the bodies may be used in the same disc space, and each may be provided according to different embodiments to distribute compressive stress or to meet other considerations. One or both of the top and bottom surfaces of the shaped body may configured to increase friction so as to maintain the body within the intervertebral space. To increase the strength and/or longevity of the implant, one or more fiber-reinforced layers may be utilized, and may use a bias-ply, a "radial" or bias-belted construction, much like arrangements used in the commercial tire industry.

17 Claims, 5 Drawing Sheets

U.S. PATENT DOCUMENTS

| | | | | |
|---|---|---|---|---|
| 5,320,644 | A | 6/1994 | Baumgartner | 623/17 |
| 5,370,697 | A | 12/1994 | Baumgartner | 623/17 |
| 5,375,823 | A | 12/1994 | Navas | 267/195 |
| 5,401,269 | A | 3/1995 | Büttner-Janz et al. | 623/17 |
| 5,425,773 | A | 6/1995 | Boyd et al. | 623/17 |
| 5,458,642 | A | 10/1995 | Beer et al. | 623/17 |
| 5,514,180 | A * | 5/1996 | Heggeness et al. | 623/17.11 |
| 5,534,028 | A | 7/1996 | Bao et al. | 623/17 |
| 5,534,030 | A | 7/1996 | Navarro et al. | 623/17 |
| 5,545,229 | A | 8/1996 | Parsons et al. | 623/17 |
| 5,556,431 | A | 9/1996 | Büttner-Janz | 623/17 |
| 5,609,635 | A | 3/1997 | Michelson | 623/17 |
| 5,645,596 | A | 7/1997 | Kim et al. | 623/17 |
| 5,645,597 | A | 7/1997 | Krapiva | 623/17 |
| 5,674,294 | A | 10/1997 | Bainville et al. | 623/17 |
| 5,674,296 | A | 10/1997 | Bryan et al. | 623/17 |
| 5,683,465 | A | 11/1997 | Shinn et al. | 623/17 |
| 5,702,450 | A | 12/1997 | Bisserie | 623/17 |
| 5,711,960 | A | 1/1998 | Shikinami | 424/426 |
| 5,716,416 | A | 2/1998 | Lin | 623/17 |
| 5,800,549 | A | 9/1998 | Bao et al. | 623/17 |
| 5,824,093 | A | 10/1998 | Ray et al. | 623/17 |
| 5,824,094 | A | 10/1998 | Serhan et al. | 623/17 |
| 5,865,845 | A | 2/1999 | Thalgott | 623/17 |
| 5,865,846 | A | 2/1999 | Bryan et al. | 623/17 |
| 5,888,226 | A | 3/1999 | Rogozinski | 623/17 |
| 5,893,889 | A | 4/1999 | Harrington | 623/17 |
| 5,899,941 | A | 5/1999 | Nishijima et al. | 623/17 |
| 5,928,284 | A | 7/1999 | Mehdizadeh | 623/17 |
| 5,964,807 | A * | 10/1999 | Gan et al. | 623/17.11 |
| 5,976,186 | A * | 11/1999 | Bao et al. | 623/17.16 |
| 6,022,376 | A * | 2/2000 | Assell et al. | 623/17.16 |
| 6,090,112 | A * | 7/2000 | Zucherman et al. | 606/61 |
| 6,110,210 | A * | 8/2000 | Norton et al. | 623/17.16 |
| 6,113,639 | A * | 9/2000 | Ray et al. | 623/17.16 |
| 6,132,465 | A * | 10/2000 | Ray et al. | 623/17.16 |
| 6,146,420 | A * | 11/2000 | McKay | 623/17.11 |
| 6,187,048 | B1 * | 2/2001 | Milner et al. | 623/17.12 |

* cited by examiner

Fig - 6A
*(STEP 1)*

Fig - 6B
*(STEP 2)*

Fig - 6C
*(STEP 3)*

Fig - 6D
*(STEP 4)*

ARTIFICIAL INTERVERTEBRAL DISC REPLACEMENT METHODS AND APPARATUS

FIELD OF THE INVENTION

This invention relates generally to surgical techniques and prosthetic components therefor and, in particular, to intervertebral disc replacement apparatus and methods of implanting the same.

BACKGROUND OF THE INVENTION

Eighty-five percent of the population will experience low back pain at some point. Fortunately, the majority of people recover from their back pain with a combination of benign neglect, rest, exercise, medication, physical therapy, or chiropractic care. A small percent of the population will suffer chronic low back pain. The cost of treatment of patients with spinal disorders plus the patient's lost productivity is estimated at 25 to 100 billion dollars annually.

Seven cervical (neck), 12 thoracic, and 5 lumbar (low back) vertebrae form the normal human spine. Intervertebral discs reside between adjacent vertebra with two exceptions. First, the articulation between the first two cervical vertebrae does not contain a disc. Second, a disc lies between the last lumbar vertebra and the sacrum (a portion of the pelvis).

The spine supports the body, and protects the spinal cord and nerves. The vertebrae of the spine are also supported by ligaments, tendons, and muscles which allow movement (flexion, extension, lateral bending, and rotation). Motion between vertebrae occurs through the disc and two facet joints. The disc lies in the front or anterior portion of the spine. The facet joints lie laterally on either side of the posterior portion of the spine.

The human intervertebral disc is an oval to kidney bean shaped structure of variable size depending on the location in the spine. The outer portion of the disc is known as the annulus fibrosis. The annulus is formed of 10 to 60 fibrous bands. The fibers in the bands alternate their direction of orientation by 30 degrees between each band. The orientation serves to control vertebral motion (one half of the bands tighten to check motion when the vertebra above or below the disc are turned in either direction). The annulus contains the nucleus. The nucleus pulpous serves to transmit and dampen axial loads. A high water content (70–80 percent) assists the nucleus in this function. The water content has a diurnal variation. The nucleus imbibes water while a person lies recumbent. Activity squeezes fluid from the disc. Nuclear material removed from the body and placed into water will imbibe water swelling to several times its normal size. The nucleus comprises roughly 50 percent of the entire disc. The nucleus contains cells (chondrocytes and fibrocytes) and proteoglycans (chondroitin sulfate and keratin sulfate). The cell density in the nucleus is on the order of 4,000 cells per micro liter.

Interestingly, the adult disc is the largest avascular structure in the human body. Given the lack of vascularity, the nucleus is not exposed to the body's immune system. Most cells in the nucleus obtain their nutrition and fluid exchange through diffusion from small blood vessels in adjacent vertebra.

The disc changes with aging. As a person ages the water content of the disc falls from approximately 85 percent at birth to 70 percent in the elderly. The ratio of chondroitin sulfate to keratin sulfate decreases with age. The ratio of chondroitin 6 sulfate to chondroitin 4 sulfate increases with age. The distinction between the annulus and the nucleus decreases with age. These changes are known as disc degeneration. Generally disc degeneration is painless.

Premature or accelerated disc degeneration is known as degenerative disc disease. A large portion of patients suffering from chronic low back pain are thought to have this condition. As the disc degenerates, the nucleus and annulus functions are compromised.

The nucleus becomes thinner and less able to handle compression loads. The annulus fibers become redundant as the nucleus shrinks. The redundant annular fibers are less effective in controlling vertebral motion. The disc pathology can result in: 1) bulging of the annulus into the spinal cord or nerves; 2) narrowing of the space between the vertebra where the nerves exit; 3) tears of the annulus as abnormal loads are transmitted to the annulus and the annulus is subjected to excessive motion between vertebra; and 4) disc herniation or extrusion of the nucleus through complete annular tears.

Current surgical treatments of disc degeneration are destructive. One group of procedures removes the nucleus or a portion of the nucleus; lumbar discectomy falls in this category. A second group of procedures destroy nuclear material; Chymopapin (an enzyme) injection, laser discectomy, and thermal therapy (heat treatment to denature proteins) fall in this category. A third group, spinal fusion procedures either remove the disc or the disc's function by connecting two or more vertebra together with bone. These destructive procedures lead to acceleration of disc degeneration. The first two groups of procedures compromise the treated disc. Fusion procedures transmit additional stress to the adjacent discs. The additional stress results in premature disc degeneration of the adjacent discs.

Prosthetic disc replacement offers many advantages. The prosthetic disc attempts to eliminate a patient's pain while preserving the disc's function. Current prosthetic disc implants, however, either replace the nucleus or the nucleus and the annulus. Both types of current procedures remove the degenerated disc component to allow room for the prosthetic component. Although the use of resilient materials has been proposed, the need remains for further improvements in the way in which prosthetic components are incorporated into the disc space, and in materials to ensure strength and longevity. Such improvements are necessary, since the prosthesis may be subjected to 100,000,000 compression cycles over the life of the implant.

SUMMARY OF THE INVENTION

This invention resides in artificial replacements for natural intervertebral discs in humans and animals. Broadly, the invention comprises a shaped body having a final volume sized to consume at least a portion of the intervertebral disc space, and a material associated with the shaped body enabling the body to cyclically compress and expand in a manner similar to the disc material being replaced. The body may be composed of a compressible material, such as polymeric urethane or other suitable elastomers, or may include a filling to impart an appropriate level of compressibility. In any case, the body preferably features some form of collapsed state permitting easier insertion, and a final state having superior and inferior surfaces preferably conformal to the concavities of the vertebral endplates. The superior and inferior surfaces may accordingly be convex, and may further include grooves, spikes, or other protrusions to maintain the body within the intervertebral space. The body may further be wedge-shaped to help restore or maintain lordosis, particularly if the prosthesis is introduced into the cervical or lumbar regions of the spine.

To enhance strength or longevity, the body may further include the use of fiber-reinforced materials on one or more outer surfaces or wall structures, as the case may be. Similar to commercial tire construction, such fiber-reinforced materials may be of a bias-ply, radial-ply or bias-belted construction. According to one configuration, an artificial disc according to the invention may further include an outer compressible member peripherally attached to a central "hub," similar, at least in concept, to the which a tire is mounted onto a wheel.

In a preferred embodiment, an artificial disc according to the invention is inflated, preferably after the body is inserted into the disc space, so that the device may assume an initial, collapsed state affording easier insertion. A gas, liquid, gel, foam or other compressible material may be used to expand the body, and the material may be introduced or otherwise provided through the use of a valve, port, syringe, or, alternatively, by way of valveless means. The body in this case is preferably a sealed unit, and may include self-sealing means in the event of a leak or rupture.

If a valve is used, it will preferably be configured so as to be accessible during implantation, enabling the surgeon to expand the device in situ. A valve may also be provided in the form of a port enabling subcutaneous post-operative inflation or re-expansion. If a gel is used as the filler material, it is preferably in the form of a hydrogel, enabling water to be imbibed and expelled to facilitate cushioning. Such a gel is preferably introduced within the body in a dehydrated state prior to implantation, with water being added to expand the material. The liquid may be added through a valve, port or hypodermic in conjunction within a sealed structure or, alternatively, at least a portion of the surface of the body, preferably the superior end or inferior surfaces, may be at least semi-porous. As a further alternative to a valveless structure, one or more reactants may be provided with the body, such that when mixed with one or more other reactants, a gas or foam is generated to expand and fill the body. As yet a further alternative, an ampule or cartridge operative to release a compressed gas or generate a gas, liquid or foam may be activated by an external source of energy such as ultrasound, heat, or other stimuli.

In terms of operative procedure, disc replacements according to the invention may be introduced through an anterior, posterior, or lateral approach using an appropriate surgical technique, including arthroscopic, laparoscopic, or microscope-assisted procedures. In the case of a non-inflatable embodiment, the prosthesis is preferably compressed to facilitate easier insertion into the disc space. The vertebrae may also be distracted, or the prosthesis may be cooled to ease implantation. More than one artificial discs according to the invention may be introduced into the same disc space, and may be arranged side-by-side laterally, or anterior to posterior. Separate flaps may be formed in the annulus fibrosis, and one or more bodies may be introduced and inflated, or allowed to expand, to at least partially distract the vertebrae to ease the insertion of additional bodies. The material of the annulus fibrosis may be reattached to maintain the disc replacement material, or synthetic bands, fabrics, or plates may be added, as required. In the event that multiple prostheses are used within a common disc space, the bodies may include interlocking shapes or structures of varying design to enhance their physical cooperation. In addition, if the replacements are arranged from anterior to posterior, devices more posterior may be smaller or of a lesser "durometer," or those placed anteriorly may be larger or less compressible (or both), again, to enhance an overall lordotic shape.

DETAILED DESCRIPTION OF THE INVENTION

This invention resides in prosthetic disc replacement devices which exhibit a desirable level of compression along the spine. Broadly, and in general terms, a replacement device according to the invention comprises a shaped body which either contains a material, or is filled with a material enabling the body to cyclically compress and expand in a manner similar to the disc material being replaced. The preferred materials forming the implant are biologically compatible natural and/or synthetic rubbers, silicones, etc., combined with biologically compatible chemicals and other materials. To enhance strength and longevity, the invention preferably incorporates one or more fiber-reinforced layers. Such layers, which may be of bias-ply, radial-ply, or belted-type arrangement similar to structures used in commercial tire design, are preferably utilized around the periphery of the body to contain outward expansion. and help limit the possibility of rupture through repeated compression/expansion cycles. The materials forming the fiber-reinforced layers also preferably contain biologically compatible fabrics composed of nylon, polyester, metal, and/or fiberglass.

In an inflatable embodiment, a prosthetic disc according to the invention is pneumatic, and is filled with air, oxygen or another suitable gas or gas mixtures. The body may also be filled with a liquid, oil, saline solution, elastomer, or gel. In either case, the prosthetic disc preferably features a valve for adding the filler material allowing the prosthetic disc to be inflated after positioning in the disc space. Hydrogels used in this embodiment are preferably sealed in the prosthetic disc in a dehydrated state. Once the prosthetic disc is placed in the spine, a liquid is added through the valve or directly through the prosthetic disc (e.g., by a needle and a syringe) to hydrate the hydrogel. U.S. Pat. Nos. 5,047,055 and 5,192,326 provide a listing of hydrogels, at least certain of which are applicable to this invention. One advantage of hydrating the gel in a sealed body is that even if pinholes form in the body, the device will still function properly, assuming biocompatible filler materials are used.

As an alternative, the body may contain one or more liquids or solids which, when mixed, produce a gas, thereby filling the body. For example, baking soda and vinegar may be used or other materials which offer a greater ratio of starting materials to the final volume, including expandable foams. In the event that a liquid is one of the components, it may be contained in an ampule of some kind which is opened upon insertion of the body into the disc space, thereby allowing the constituent materials to mix. In a different arrangement, the body may include some form of structure with a window or other port which becomes compromised in the presence of externally supplied energy in the form of ultrasound, heat, etc., thereby allowing a foam to expand, reactants to mix, and so forth.

According to a different preferred embodiment, the prosthetic disc does not contain a cavity, but is constructed of a biologically compatible yet compressible material such as silicone or rubber. The preferred material would exhibit the same properties as advanced polymetric urethane of the type used in non-pneumatic tires. In this embodiment, the prosthesis would not be inflated or imbibe fluid to expand. Rather, the prosthesis would preferably be compressed or deformed prior to insertion into the disc space.

Regardless of the embodiment, the prosthetic disc according to the invention would be inserted through the annulus fibrosis in a surgical procedure. The surgeon would cut a flap or hole in the annulus, and the degenerated nucleus pulpous would be removed according to the standard techniques. One, two, or more prosthesis according to the invention would then be introduced into the disc space, depending upon the location in the body, patient physiology, and so forth.

Although the size examples shown in the drawings may be implied as applicable to human lumbar disc, the prosthesis according to the invention may also be provided for cervical and thoracic discs as well as other joints of the body or animals, through appropriate geometrical scaling. In addition, although it is implied that when multiple prosthesis are used, the same embodiment of the prosthesis would be introduced into the disc space, this is not necessarily always the case, since the various embodiments disclosed herein may be mixed and matched, even within the same disc space, depending upon the physical arrangement.

The prostheses could be inserted through the posterior, anterior, or lateral portion of the intervertebral disc by standard surgical procedures. In each case, the prosthesis would come in various sizes to accommodate different size discs. If two prostheses are used in one disc space, each prosthesis would measure approximately 10–30 mm×10–20 mm×5–20 mm. If one prosthesis is used, it would measure approximately 10–30 mm×20–40 mm×5–20 mm. The prostheses could be used in cervical, thoracic, or lumbar discs of animals and humans. In addition the device could be used in other joints, including the ankle.

Figure 1A:
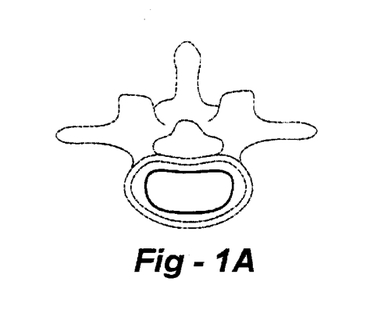
FIG. 1A is a simplified drawing illustrating the implantation of one prosthesis according to the invention as viewed upwardly toward the head of the recipient.
Figures 1B, 1C:
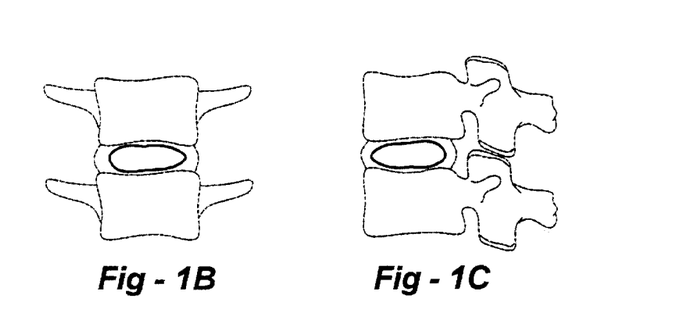
FIG. 1B is a simplified drawing of the single prosthesis of FIG. 1A as seen from the back.
FIG. 1C is a simplified drawing of the single prosthesis embodiment of FIG. 1A, as viewed from the side.
Figure 2A:
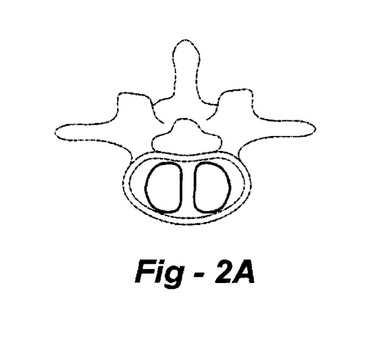
FIG. 2A is a simplified drawing of a disc replacement according to the invention utilizing two prosthesis per disc as viewed upwardly toward the head of the recipient.
Figures 2B, 2C:
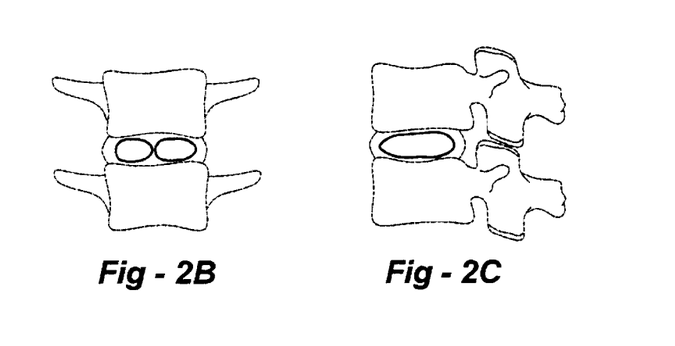
FIG. 2B is a simplified drawing of the two prosthesis embodiment of FIG. 2A as viewed front to back.
FIG. 2C is a simplified drawing of the embodiment of FIG. 2A as viewed from the side.
Figure 3A:
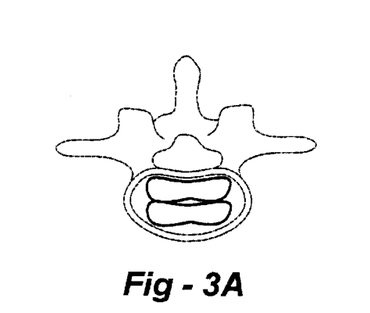
FIG. 3A is a simplified drawing of an alternative configuration utilizing two prosthesis per disc placed laterally.
Figures 3B, 3C:
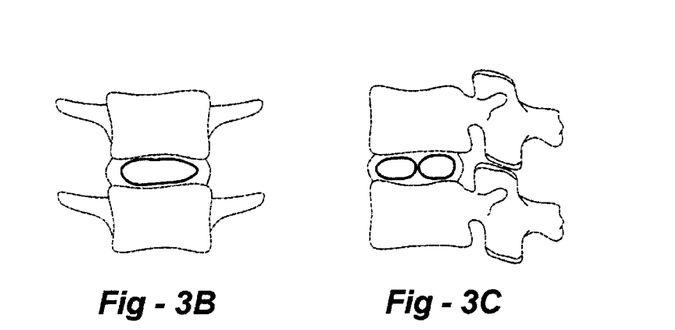
FIG. 3B is a simplified drawing of the lateral placement of FIG. 3A as viewed from the back.
FIG. 3C is a simplified drawing of the lateral placement of FIG. 3A as viewed front to side.

FIG. 1A is a simplified drawing which illustrates the implantation of one prosthesis according to the invention as viewed upwardly toward the head of the recipient. FIG. 1B is a simplified drawing of the single prosthesis as seen from the back, and FIG. 1C is a view from the side. FIG. 2A is a simplified drawing of the invention utilizing two prosthesis per disc as viewed upwardly toward the head of the: recipient. FIG. 2B is a simplified drawing as viewed front to back and FIG. 2C is a simplified drawing as viewed from the side. The prosthesis may be placed front to back or back to front, depending upon if entry is made through the back or abdomen of the patient. FIG. 3A is a simplified drawing of an alternative configuration utilizing two prosthesis per disc placed laterally. FIG. 3B is a view from the back, and FIG. 3C is a simplified drawing of a lateral placement as viewed front to side.

Particularly when a single prosthesis is used, it will preferably feature convex superior and inferior surfaces so as to conform to the concavities of the vertebral end plates. In addition, the prosthesis may be wedge-shaped, such that the anterior surface is taller than the posterior surface. Such a shape is particularly beneficial in restoring or. maintaining lordosis in the cervical and lumbar region of the spine. In the event that a plurality of prostheses are positioned anterior to posterior, as shown in FIGS. 3A–3C, it may be advantageous to place thicker or less resilient devices anteriorally, with devices having a smaller cross-section or more compressible durometer posteriorally.

Figure 4A:
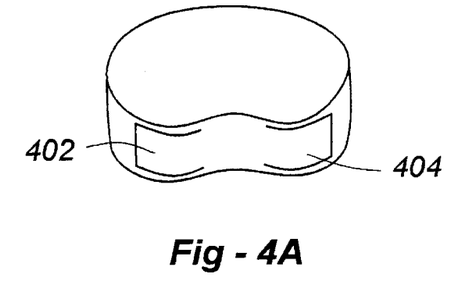
FIG. 4A is an oblique representation of the way in which one or more flaps may be used to insert a prosthesis into a retainer according to the invention.
Figure 4B:
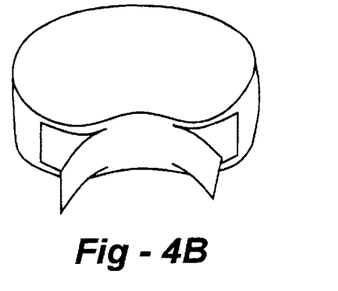
FIG. 4B is a drawing of the arrangement of FIG. 4A, but with the annular flaps opened.
Figure 4C:
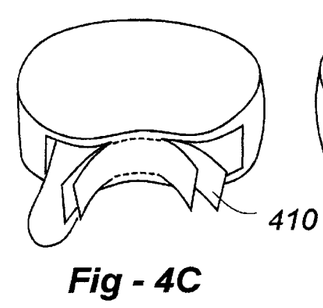
FIG. 4C is a drawing which illustrates the alternative use of a band to close off one or more annular flaps used to introduce an intravertebral disc replacement according to the invention.
Figure 4D:
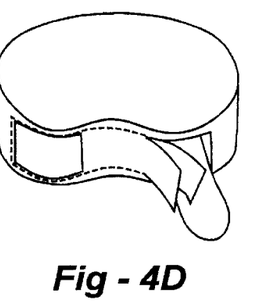
FIG. 4D which is a drawing which furthers the configuration shown in FIG. 4C, wherein a second intervertebral disc replacement is being introduced.
Figure 4E:
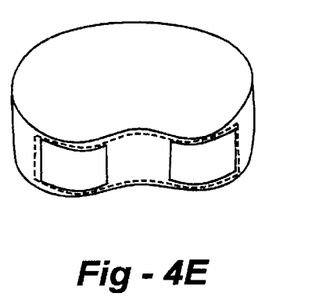
FIG. 4E is a drawing which subsequent to that of FIG. 4D, wherein the band is used to close off a pair of annular flaps.

In the case of two prosthesis, two annular flaps 402 and 404 would preferably be. created as shown in FIG. 4A. FIG. 4B is a drawing which shows the annular flaps in an open state. A prosthesis or prostheses may also be inserted through one annular flap. In addition, the prosthesis or prostheses may be inserted through the annular window that follows a procedure to remove a herniated nucleus pulpous. If annular flaps are formed, they may be sewn or sealed closed after insertion of the artificial disc or discs. The prosthetic disc or discs could restore a collapsed disc space by inflation of the prosthesis or prostheses. The vertebrae may also be distracted to restore normal disc height and aid the insertion of the prosthesis or prostheses, mechanically. As shown in FIGS. 4C–4E, a malleable band 410 of flexible plastic, metal or other material may be inserted through the annular flaps as shown, a material with a shape memory may be beneficial for such purpose. FIG. 4C shows a situation wherein a collapsed replacement is inserted into one of the two openings, and FIG. 4D shows a disc replacement member according to the invention being inserted into the other opening. FIG. 4E shows how the band of material 410 would be used to close both openings through suturing or other appropriate surgical techniques.

Figure 4F:
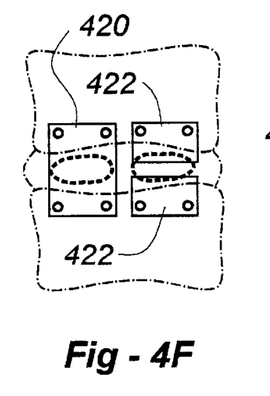
FIG. 4F is a drawing which shows how a flexible patch or retaining pieces may be used to close off an annular flap according to the invention.
Figure 4G:
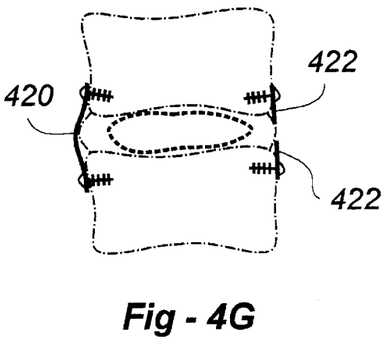
FIG. 4G which shows the flexible material and retaining pieces from a side-view perspective.
Figure 4H:
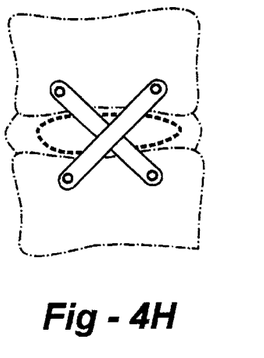
FIG. 4H illustrates an alternative use of crisscross bands for use in annular flap closure.

FIGS. 4F through 4H illustrate alternative approaches, wherein panels may be attached to adjacent vertebrae for the purpose of retaining disc replacement material. As shown in the front-view drawing of FIG. 4F, a flexible piece of material 420 may be attached to adjacent vertebrae in the form of a rectangular shape or cords. Such a material would permit normal movement of the spine, and may be attached to upper and lower vertebrae through any appropriate known technique for fixation. A cloth fabric, such as Gore-Tex® or Dacron®, or a mesh screen such as nylon may be attached to the adjacent vertebrae as shown, allowing normal movement. Such a technique would be used primarily when the prosthetic disc is placed from an anterior approach to the spine, whether cervical thoracic or lumbar, and would help to restore normal annular function. As an alternative to a flexible fabric or screen, one or more retaining members 422 may alternatively be utilized. Such a member, which may be plastic, metal or other suitable material, would be attached to one or both of the adjacent vertebrae as shown. FIG. 4G is a drawing which shows the fabric 420 in panels 422, as viewed from the side. FIG. 4H illustrates how materials may be applied in criss-cross fashion, in the form of bands, for example.

Mechanical distraction of the vertebra may also be used for disc replacement. U.S. Pat. No. 5,824,093, for example, describes an air jack that could be inserted through one of the flaps. Once the distraction is achieved, a prosthesis is inserted through the other annular flap. Air jacks of the type disclosed in the '093 patent may also be inserted through both annular flaps to achieve symmetric distraction. When properly distracted, one air jack may be deflated and removed. The first prosthesis would be inserted into the space formerly occupied by the air jack. After the first prosthesis is inserted, the second air jack would be deflated and removed. A second prosthesis would be inserted into the remaining disc space. A crank scissors jack could also be used to distract the vertebrae.

The intra-discal position of the prosthesis or prostheses may be maintained in a number of ways. First, the prosthesis diameter is larger in the center portion than the periphery. Second, the prosthesis expands after insertion through the annular opening. Third, the majority of annulus fibrosis is preserved. Fourth, the prosthesis exerts constant pressure on the adjacent vertebrae, securing a tight fit. Fifth, the vertebrae may be distracted so as to enlarge the disc space prior to inserting the prosthesis.

Figure 5A:
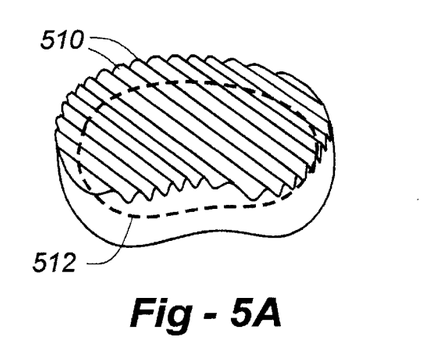
FIG. 5A is a drawing seen from an oblique perspective illustrating the use of an inflatable body which may include transverse grooves to increase friction fit within the disc space.
Figure 5B:
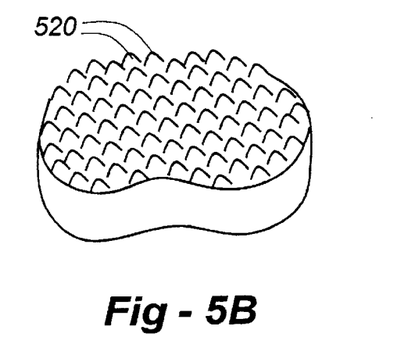
FIG. 5B is a drawing which illustrates the way in which bumps or protrusions may be employed to increase friction fit.
Figure 5C:
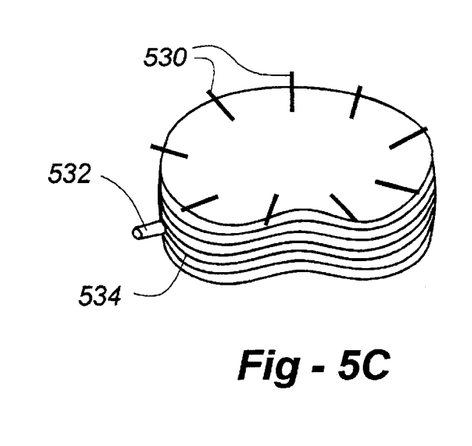
FIG. 5C is an oblique drawing of an alternative arrangement including angled projections to maintain an intervertebral disc replacement according to the invention within a disc space.

When the distraction is released after prosthesis insertion, the tension placed on the annular fibers will serve to hold the prosthesis in position. As depicted in FIGS. 5A through 5C, the prosthesis may contain either grooves 510, bumps 520, or to increase the friction against metal spikes 530, preferably placed on the superior and inferior surfaces of the prosthesis, to assist in keeping the body in place. Such protrusions would preferably be angled to allow for easy insertion while, at the same time, helping to prevent extrusion of the prosthesis through the annular window. Additional devices may also be used, similar or identical to those described in co-pending U.S. patent application Ser. No. 09/322,516, the entire contents of which are incorporated herein by reference.

FIGS. 6A–6D illustrate a preferred way an artificial disc replacement device according to the invention may be covered with one or more layers of fiber-reinforced material. Such layers may contain any biologically compatible fabrics composed of nylon, polyester, metal and/or fiberglass, or other suitable materials. One advantage of using metal fibers is that the belts could be seen on x-rays, thereby showing the position of the implant(s) by radiograph.

Figure 6A:
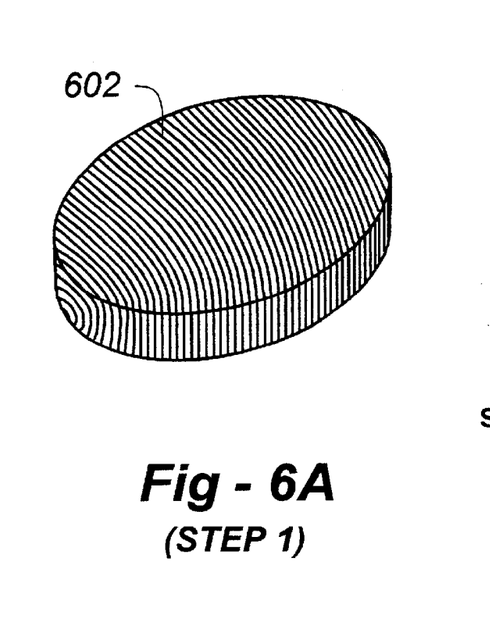
FIG. 6A is an oblique drawing which shows a first fiber-reinforced layer applied to a shaped body according to the invention.
Figure 7:
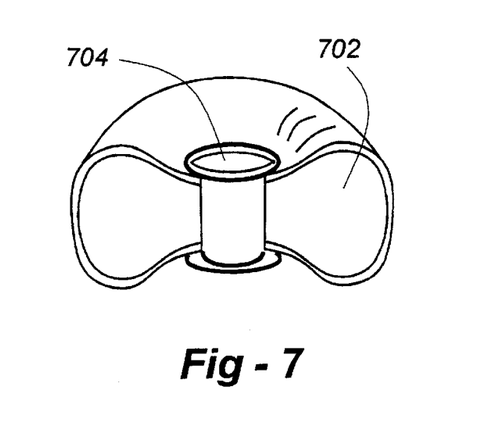
FIG. 7 is a drawing which shows an alternative embodiment of the invention wherein a resilient peripheral member is bonded to a central core.

FIG. 6A illustrates a first step wherein wherein a first ply 602 is applied having fibers with an orientation across the body, as shown. If only a single fiber-reinforced layer is utilized, the orientation of the fibers may be particularly important, depending upon whether a single prosthesis or multiple implants are used. For example, it may be advantageous to have fibers running from a central portion of the superior surface around the sides of the device to a central portion of the inferior surface. Such an arrangement might be particularly advantageous if the wheel/hub structure of FIG. 7 is chosen.

Figure 6B:
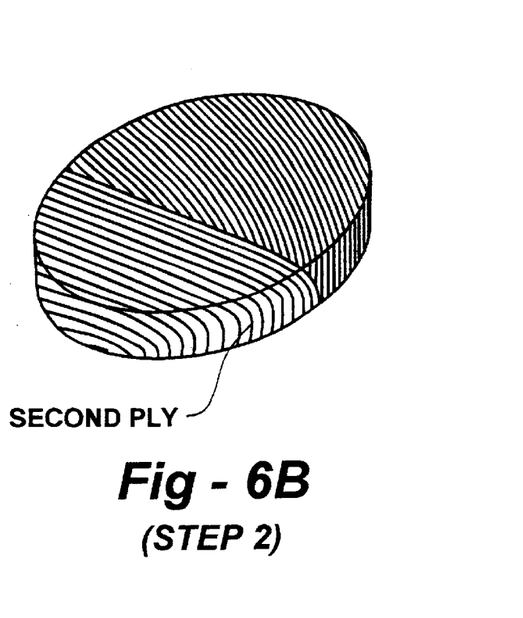
FIG. 6B illustrates the application of a second ply having fibers oriented at an angle relative to the first ply.

However, if additional ply layers are added, as shown in FIG. 6B, the orientation of the fibers are preferably made at angles with respect to one another, as is done in bias-ply tire designs. For example, the fibers of each ply would be oriented at angles up to 90 degrees relative to one another, where possible, depending upon the shape of the device.

Figures 6C, 6D:
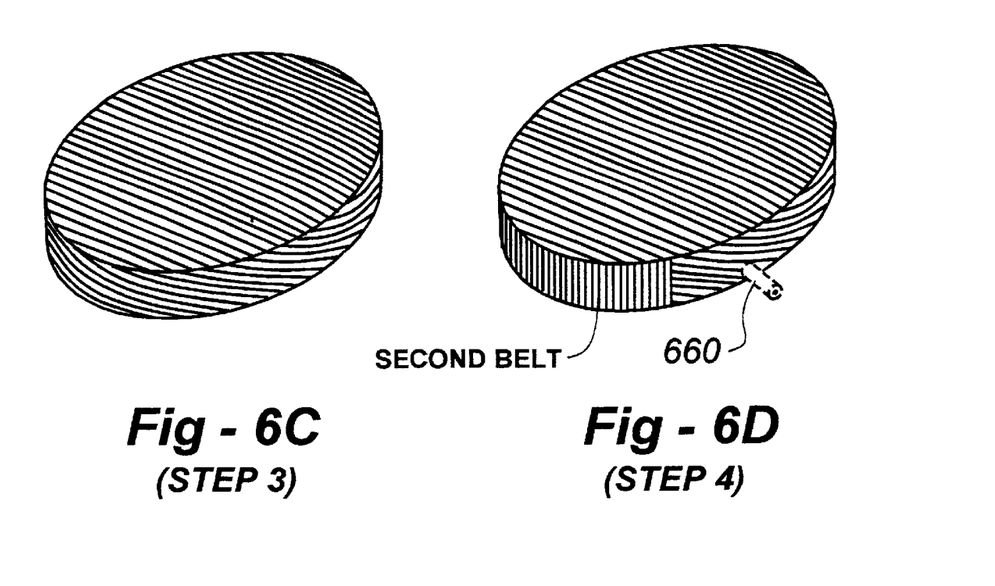
FIG. 6C illustrates a third step wherein a first radial belt is applied around the periphery of the body.
FIG. 6D illustrates a fourth step wherein a second radial belt is applied such that its fibers are oriented at an angle with respect to the fibers of the first radial belt.

Just as a plurality of fiber-reinforced layers is optional according to the invention, so too is the addition of belts around the periphery of the device, as shown in FIGS. 6C and 6D. Such "radial" belts are preferred, however, in that they would impart additional strength and enable the device to withstand the millions of compression cycles typically seen during the life of the implant. As shown in FIG. 6C, a first belt would be added around the periphery of the side wall of the device, as shown, again, with the orientation of the fibers of the belt being angled with respect to those of the underlying ply, where practical. As shown in FIG. 6D, a second radial belt may be added, preferably having fibers at an angle relative to the first belt, thereby strengthening the device that much further.

It must be noted that the bias ply and radial belted arrangements of FIGS. 6A–6D may be used with a device which is externally inflatable or expandable according to the invention, or in conjunction with alternative embodiment discloses herein wherein the device is sealed and preferably compressible prior to insertion. Accordingly, the valve 660 is optional in a sense that it would be used only in conjunction with the inflatable or expandable embodiments of the invention. If the device is manufactured in a pre-inflated and valveless configuration, as a further alternative, the air, liquid, gel or other material may be injected into the cavity of the device after the application of the first ply layer. A needle may be used to introduce the material, and may be directed into the device along the same orientation of the ply layer, thereby minimizing ply damage. After inflation to an appropriate pressure, the additional plies and belts may be added so as to seal any perforation made by the needle or syringe used to introduce the filler material. As yet a further alternative, the cavity within the first ply or between ply/belt layers may contain a self-sealing polymer to "heal" any punctures that might occur during filling or subsequent reliance on the device once implanted.

The prosthesis may further contain a solid center portion constructed of metal, plastic or other suitable material, much like the way in which a tire is mounted onto a wheel, as shown in FIG. 7. Such an embodiment could allow a dehydrated hydrogel or other material to be added to the prosthetic "tire" 702 prior to be mounted on the central "wheel" portion 704. One benefit of this arrangement is that the wheel portion 704 may be stronger and more durable than if the tire portion 702 were used alone, as shown generally in FIGS. 5 and 6. Indeed, such a prosthesis could contain a biologically compatible self-sealing liquid or polymer similar to that used in the tire industry. In terms of an outer material, a polyolefin rubber may be used, particularly if biocompatible and fatigue resistant. One candidate is described in U.S. Pat. No. 5,071,437, which is sold by the Goodyear Tire and Rubber Company under the trademark Hexsyn®.

Figure 8A:
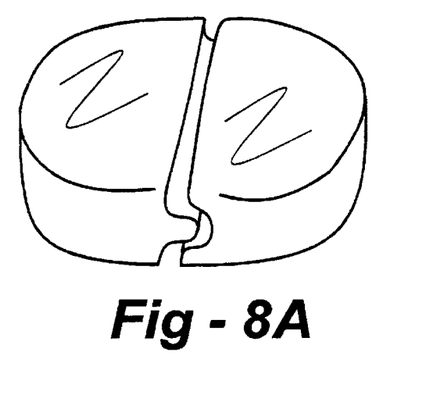
FIG. 8A is a top-view drawing which shows how multiple disc replacement components may be interlocked according to the invention.
Figure 8B:
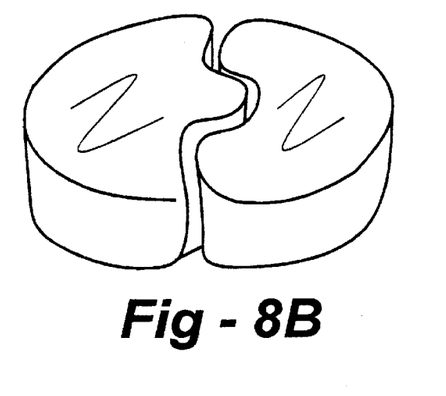
FIG. 8B illustrates a different interlocking scheme.
Figure 8C:
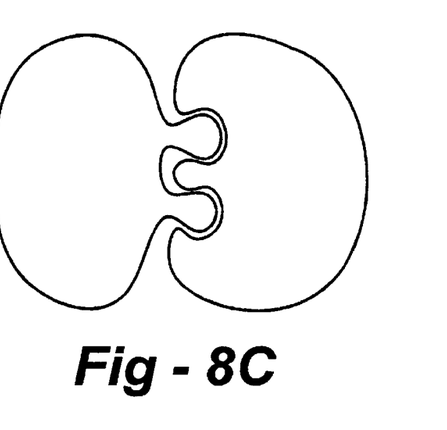
FIG. 8C illustrates yet a different interlocking scheme having one or more plugs and receptacles.
Figure 8D:
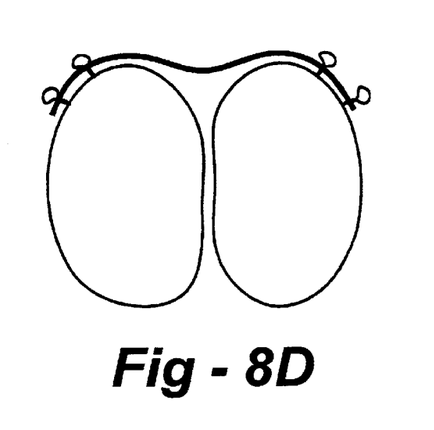
FIG. 8D illustrates yet a further technique for interconnecting multiple intervertebral disc replacement parts according to the invention.

Generally, only one prosthetic disc would be placed into the disc space in the cervical region of the spine. If multiple prostheses are used, as shown in FIGS. 2A through 3C and 4F, the shapes may further include an interlocking structure to help hold them in place, at least relative to one another. FIG. 8A shows a lateral scheme for interlocking adjoining shaped bodies, whereas FIG. 8B illustrates a vertical arrangement much like puzzle pieces. Truly interlocking mechanisms may also be utilized, as shown in FIG. 8C, which incorporates knobs received by receptacles, and FIG. 8E, which illustrates a band of material which is fastened to adjacent devices through any appropriate form of fastener.

I claim:

1. An artificial replacement for a natural intervertebral disc, comprising:
    a sealed body having a non-expanded state and an expanded state with a final volume sized to consume at least a portion of an intervertebral disc space; and
    wherein the body includes a fiber-reinforced wall structure having a bias-ply, radial, or bias-belted construction.

2. The artificial disc replacement of claim 1, further including a valve disposed on the body to receive a filler material for expanding the body.

3. The artificial disc replacement of claim 2, wherein the filler material is a gas, liquid or gel.

4. The artificial disc replacement of claim 3, wherein the gel is a hydrogel.

5. The artificial disc replacement of claim 1, wherein the sealed body has a surface with one or more features to maintain the body within the disc space.

6. The artificial disc replacement of claim 1, wherein the fiber-reinforced wall structure includes one or more biologically compatible fabrics composed of nylon, polyester, metal, fiberglass, or a combination thereof.

7. An artificial replacement for a natural intervertebral disc, comprising:
    a sealed, expandable body having a final volume sized to consume at least a portion of an intervertebral disc space; and
    wherein the body assumes a convex, lordotic shape according to the final volume.

8. An artificial replacement for a natural intervertebral disc, comprising:
    a sealed, expandable body having a final volume sized to consume at least a portion of an intervertebral disc space; and
    a central hub to which the body is peripherally attached.

9. The artificial disc replacement of claim 1, wherein the body further features moisture-permeable superior and inferior surfaces.

10. A method of filling at least a portion of an intervertebral disc space to treat disc degeneration, comprising the steps of:
    providing an artificial disc replacement in the form of a shaped body having an initial volume which is smaller than the final volume;
    cutting a hole or flap in the annulus of the disc,
    inserting the shaped body in the initial volume into the space through the flap;
    introducing the shaped body having the initial volume into the disc space;
    expanding or allowing the body to expand into the final volume so as to fill at least a portion of the disc space; and
    closing the flap.

11. The method of claim 10, wherein:
    the filling of the shaped body is a gas, a liquid, or a gel; and
    the method includes the step of inflating the shaped body with the gas, liquid or gel after the body is introduced into the disc space until the body assumes the final volume.

12. The method of claim 10, wherein:
    the shaped body is water-permeable and filled with a hydrogel; and
    the method includes the step introducing the body into the disc space in a dehydrated state so as to imbibe water and assume the final volume.

13. The method of claim 10, further including the steps of:
    cutting two adjacent holes or flaps in the annulus of the disc;
    inserting a mechanical distraction tool into one of the holes or flaps and distracting the vertebrae above and below the disc space using the tool;
    inserting one of the shaped bodies in the initial volume into the space through the other hole or flap;
    removing the mechanical distraction tool; and
    inserting the other shaped bodies in the initial volume into the space previously occupied by the mechanical distraction tool.

14. The method of claim 12, further including the steps of:
    providing a shaped body having one or more liquids or solids disposed therein which, when mixed, generate a gas operative to expand the body; and
    causing the materials within the body to mix after the body has been introduced into the disc space.

15. The artificial replacement for a natural intervertebral disc of claim 1, including two or more shaped bodies appropriately sized to occupy the same disc space; and
    wherein the bodies feature an interlocking outer body shape enabling them to be coupled to one another.

16. The artificial replacement for a natural intervertebral disc of claim 1, wherein the body is disposed between upper and lower vertebrae, and the replacement further includes:
   an element attached to one or both of the upper and lower vertebrae for maintaining the body within the disc space.

17. The artificial replacement for a natural intervertebral disc of claim 16, wherein the element attached to one or both of the upper and lower vertebrae includes one or more resilient straps.

* * * * *